(12) United States Patent
Beck et al.

(10) Patent No.: US 8,751,020 B2
(45) Date of Patent: *Jun. 10, 2014

(54) ELECTRODE ARRANGEMENT

(71) Applicant: cerbomed GmbH, Erlangen (DE)

(72) Inventors: Christoph Beck, Moehrendorf (DE);
Stefan Baer, Cadolzburg (DE)

(73) Assignee: Cerbomed GmbH, Erlangen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/915,762

(22) Filed: Jun. 12, 2013

(65) Prior Publication Data
US 2013/0274848 A1 Oct. 17, 2013

Related U.S. Application Data

(63) Continuation of application No. PCT/EP2011/005934, filed on Nov. 25, 2011.

(30) Foreign Application Priority Data

Dec. 12, 2010 (DE) .......................... 10 2010 054 165

(51) Int. Cl.
*A61N 1/00* (2006.01)

(52) U.S. Cl.
USPC ........................................ 607/139

(58) Field of Classification Search
USPC .......................................... 607/139
See application file for complete search history.

(56) References Cited

U.S. PATENT DOCUMENTS 5,514,175 A 5/1996 Kim

FOREIGN PATENT DOCUMENTS

| DE | 102005003735 A1 | 7/2006 |
| WO | 2007134804 A1 | 11/2007 |
| WO | 2008042863 A2 | 4/2008 |
| WO | 2009155516 A2 | 12/2009 |

*Primary Examiner* — Robert N Wieland
(74) *Attorney, Agent, or Firm* — Lucas & Mercanti, LLP

(57) ABSTRACT

The invention relates to a electrode arrangement (1) for the application of a transcutaneous electric stimulation stimulus onto the surface of a section of the human ear (2), which comprises a holding element (3) to be arranged at or in the ear (2) as well as at least on electrode (4, 5), which electrode (4, 5) is arranged in an electrode carrier (6). To allow a simple and comfortable application of the electrode arrangement at the ear and to influence the hearing during wearing of the electrode arrangement as little as possible the invention suggests that the holding element (3) comprises a linear guide (7) in which a holding bar (8) is arranged linear movably in the direction of a longitudinal axis (L) of the holding element (3), wherein the electrode carrier (6) is arranged at the holding bar (8).

15 Claims, 9 Drawing Sheets

ELECTRODE ARRANGEMENT

CROSS-REFERENCE TO RELATED APPLICATIONS

Figure 1:
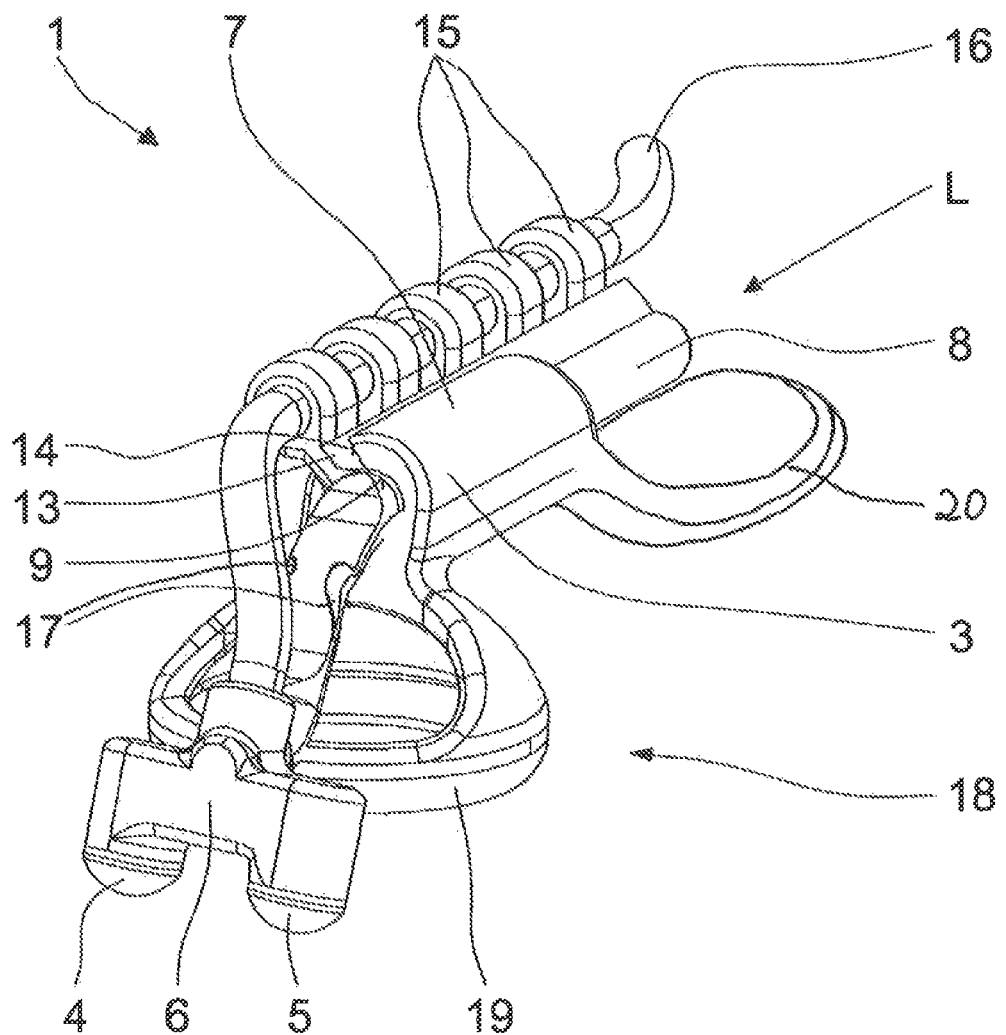

This application is a Continuation of PCT/EP2011/005934 filed Nov. 25, 2011, which in turn claims the priority of DE 10 2010 054 165.6 filed Dec. 12, 2010, the priority of both applications is hereby claimed and both applications are incorporated by reference herein.

The invention relates to an electrode arrangement for the application of a transcutaneous electric stimulation stimulus onto the surface of a section of the human ear, which comprises a holding element to be arranged at or in the ear as well as at least on electrode, which electrode is arranged in an electrode carrier.

It is generally known to take influence on the neurophysiological and neuroelectrical quality through invasive and non-invasive stimulation of the nerves and thereby on the function of the simulated nerves. Hereby different conditions of sickness can be treated. Numerous devices exist both for the invasive and the non-invasive stimulation.

The present invention is basing upon the method of the transcutaneous electrical stimulation of the nerves. At this method pulse currents of different current forms, amplitudes, pulse durations and frequencies are administered through the skin on different nerves and change their status parameter in an advantageous way.

An electrode arrangement of the kind mentioned above is known from EP 2 026 872 B1. Here, an electrode arrangement is described, which comprises a housing which can be completely arranged in the Pinna (ear conch). From this two bended, wire-shaped sections extend, which are designed as spring elastically holdings. In doing so the electrode arrangement can be brought into the correct position into the Pinna through soft pinching, so that the ear canal can be impinged with a transcutaneous stimulation impulse. Other stimulation appliances are disclosed in DE 10 2005 003 735 A1 and in U.S. Pat. No. 5,514,175.

Another stimulation device is disclosed in WO 2009/155516 A2, wherein the electrode holding is designed like an ear-phone. WO 2008/042863 A2 describes a stimulation device which uses an implanted electrode.

Although the above mentioned pre-known electrode arrangement already leads to good treatment results, some disadvantages of the arrangement have occurred in experience.

As the electrode arrangements with their electrodes have to be built very small, as naturally conditioned, the mechanical stability of the necessary connections is not yet dissolved optimally, particularly of the electrodes with their connection cables. Hence it can come to an insufficient holding of the electrodes, which will be benefited thereby, that a very soft cuddly material (particularly silicon) has to be used for the holding to achieve a sufficient wearing comfort. From time to time it comes to irreparable damages of the contacts of the electrodes due to a respective mechanical strain of the electrode arrangement during insertion into the ear canal.

Furthermore, it has been realized as disadvantageous, that it is difficult to adjust an electrode arrangement, which electrode arrangement is already in existence, if applicable onto the individual size of the Pinna and generally of the ear respectively. This leads occasionally to high effort during the insertion of the electrode arrangement and to a not optimal wearing comfort respectively.

It is also disadvantageous at some of the pre-known electrode arrangements, that the hearing can be influenced negatively.

Thus, it is an object of the invention, to further develop an electrode arrangement of the generic kind in such a manner, that the mentioned disadvantages can be overcome. Thus, it shall be proposed an electrode arrangement, by which also higher mechanical strains can be transferred safely, wherein the electrodes can be held securely in position. Specifically, in doing so a simple possibility shall be created to adjust the electrode arrangement at different sizes of the ear. The insertion of the electrode arrangement shall be possible in an easy and comfortable way. Thereby, the hearing shall be influenced negatively as less as possible during carrying of the electrode arrangement.

The solution of this object by the invention is characterized in that the holding element comprises a resting part, which resting part is designed and provided for the application onto the Cavum conchae of the ear and that the holding element comprises a linear guide in which a holding bar is arranged linear movably in the direction of a longitudinal axis of the holding element, wherein the electrode carrier is arranged at the holding bar.

The electrode carrier is mostly arranged at an axial end of the holding bar.

The electrode carrier, designed especially as electrode head, comprises preferably at least one stimulation electrode and at least one reference electrode.

The linear guide of the holding element can be formed by a recess which recess has a constant shape, especially a circular shape, along the longitudinal axis in a section perpendicular to the longitudinal axis; the holding bar comprises then preferably a circular shaped cross section at least along a part of its extension.

Furthermore, latching means can be effectively arranged between the linear guide and the holding bar, so that the holding bar can be arranged lockable relatively to the linear guide along the longitudinal axis in predetermined relative positions. The latching means can comprise at least one groove-shaped recess within the linear guide as well as at least one protrusion within the holding bar, which protrusion extends radial outward. The protrusions are designed preferably as a wave path with a plurality of radial elevations.

Furthermore, additively or alternatively fixation means can also be arranged which block the relative linear position between the holding element and the holding bar, i. e. which prevent a linear movement by means of the linear guide.

Furthermore, spring means can be effectively arranged between the linear guide and the holding bar, so that the holding bar can be biased elastically relative to the linear guide in the direction of the longitudinal axis.

Furthermore, means can be arranged for preventing of rotation of the holding bar relatively to the linear guide around the longitudinal axis. Those means can be formed by a lateral extension, which lateral extension is radial extending from the holding bar, wherein in the linear guide a corresponding recess for the lateral extension is arranged. The lateral extension as well as the recess can have a square form in a section perpendicular to the longitudinal axis. Holding means for an electrical cable can be arranged at the end of the lateral extension which is remote from the holding bar, which cable is in electrical connection at least with one electrode. The holding means are preferably designed as at least one holding ring for the cable.

The holding bar including the lateral extension and if applicable the holding means are preferably designed as one-piece injection molding part.

The holding bar has preferably a S-form design in its axial end region, in which end region the electrode carrier is arranged. It can be reinforced in its axial end region with a spring element, particularly with a spring wire or a leaf spring, in which end region the electrode carrier is arranged to ensure a sufficient elasticity of the electrode carrier relatively to the holding element.

Generally, it can be provided that by respective measures a desired elasticity of the electrode carrier relatively to the holding element is obtained. The mentioned integration of a spring element is only one possibility. Also, it can be reached by suitable design measures that the elasticity and spring constant respectively are in a desired range. So it is possible for example that a section of the holding bar is reinforced by a metallic spring leaf and simultaneously to reduce the material of the holding bar in this section or to do totally without it. The leaf spring allows a spring elasticity in a defined direction, while the connection between the holding element and the electrode carrier remains stiffer in other load directions.

From the above comments it is to be understood that the term "holding element" has to be interpreted here widely and is not at all restricted to classical rod-shaped structures.

The holding bar can comprise at least one collateral notch or at least one collateral insection in its axial end region, in which end region the electrode carrier is arranged, to reduce the bending stiffness of the holding bar in the axial end region around a direction, which is perpendicular to the longitudinal axis. The adaption of the electrode carrier on the topography of the surface of the skin to be stimulated is thereby facilitated.

The resting part has preferably a ring-shaped section, particularly a circular ring-shaped section or an oval ring section.

The ring-shaped section of the resting part can comprise an interception at at least one circumferential position. By doing so it can be reached that a facilitated adaption of the circular-shaped section at the bearing region in the ear is given at different sizes of the ear.

An alternative or additive possibility to adapt the size and/or form of the ring-shaped section to individual requirements it that a ring-like cover element (e. g. a rubber ring) is mounted onto the outer circumference of the ring-shaped section. This enlarges the outer circumference of the ring-shaped section. It is also possible that the cover element has an asymmetric form so that herewith also the outer shape of the ring-shaped section can be modified to obtain a better accurately fitting of the electrode arrangement in the ear, i. e. the adaptability of the electrode arrangement is improved.

At least the ring-shaped section of the resting part, eventually also the mentioned cover element, can consist of an elastically, soft material, particularly of a biocompatible elastomeric material, preferably of silicon or of a material, which comprises silicon.

Furthermore, the holding element can comprise a cheek rest, which cheek rest is arranged at the holding element at the end of the electrode arrangement remote from the electrode carrier. Thereby, an improved support of the electrode arrangement can be obtained.

The at least one electrode is preferably at least partially embedded into the material of the electrode carrier, particularly injection-molded by an injection molding process.

The at least one electrode comprises preferably a contact section and a pin-shaped anchoring section, wherein at least one insertion is arranged between the contact section and the anchoring section. The pin-shaped anchoring section can thereby comprise a flat area or a recess or a protrusion at at least one circumferential position to constitute a prevention of rotation during the embedding into the material of the electrode carrier.

The pieces of the electrode arrangement consist preferably—as long as a contact to the skin is given—of a soft material, wherein it is thought especially at an elastomer material, particularly at silicon or a material, which contains silicon. However, the electrode head and the holding bar consist preferably of a thermoplastic or thermosetting plastic material, for example also of polyurethane.

The stimulation electrode(s) and the reference electrode(s) can be embedded at least partially into the material of the electrode head. They can be put into the injection molding tool during injection molding of the electrode head and are then injection moulded by the material of the electrode head.

It shall be mentioned, that the proposed electrode arrangement can comprise also only one electrode. It is possible, that a separate reference electrode will be used, which reference electrode will be placed outside of the electrode arrangement (e. g. behind the ear) and which stands in electrical contact with the stimulation device. It is also possible, that indeed two or more electrodes exist—as in the embodiment—but that a further reference electrode is used outside of the electrode arrangement.

A further development provides, that the electrode arrangement is provided with an acoustical giver (loud speaker), preferably in the area of the restring part and its ring-shaped section respectively. With that it will be possible, to feed the user of the electrode arrangement also acoustical signals during the electro stimulation, which can also occur for reasons of entertainment.

It is advantageous, that a pretty stable construction be achieved by the proposed embodiment of the electrode arrangement without influencing the wearing comfort negatively. The electrodes will be kept stable and reliable in the required position, as they are arranged via the holding bar at the relatively stable holding element.

It is incidentally possible due to the two-part construction to combine the holding bar including the electrode head on the one side with the holding bar on the other side. That opens the possibility to combine different sized elements with each other. A preferred supply configuration provides therefore more than one holding bar including electrode head and/or more than one holding element. The user can then chose and connect the elements with the size which is optimal for his proportion to have an optimal fitting electrode arrangement in provision.

So, in particular the holding elements can be adjusted at different sized ears and different ear forms respectively in a very simple way. The electrode head and the electrodes respectively lie thereby always with a defined pressure on the skin.

Figure 2:
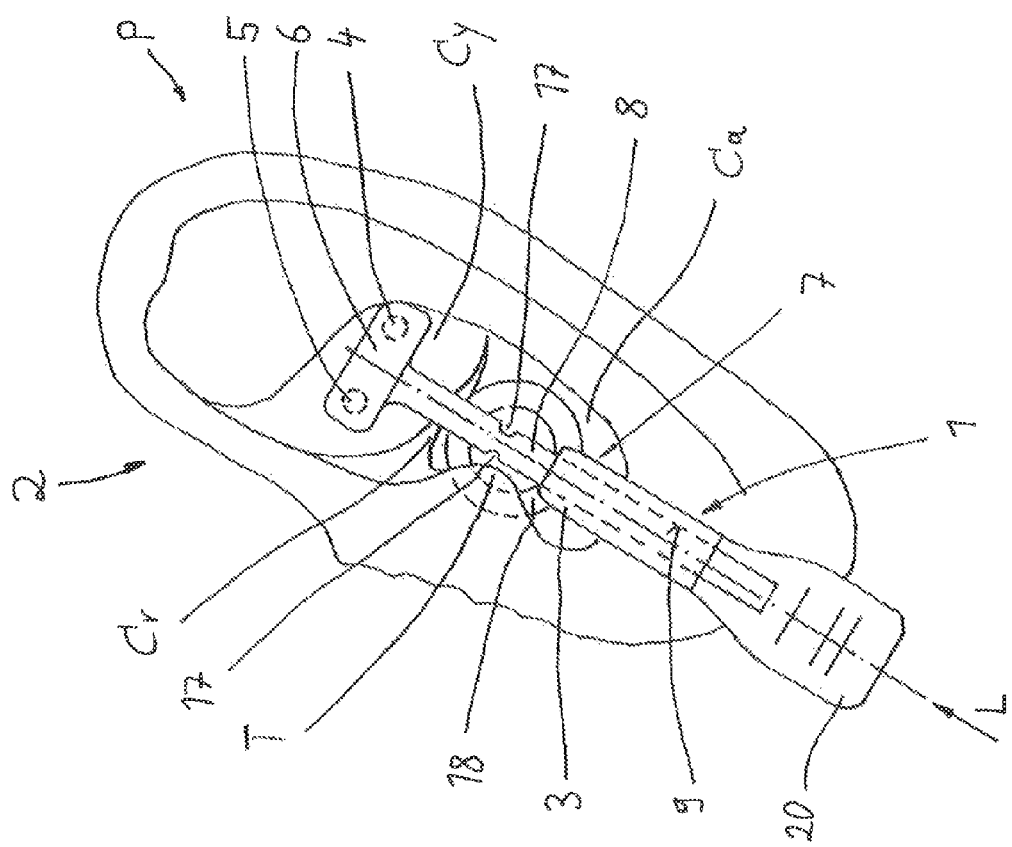
Figure 3:
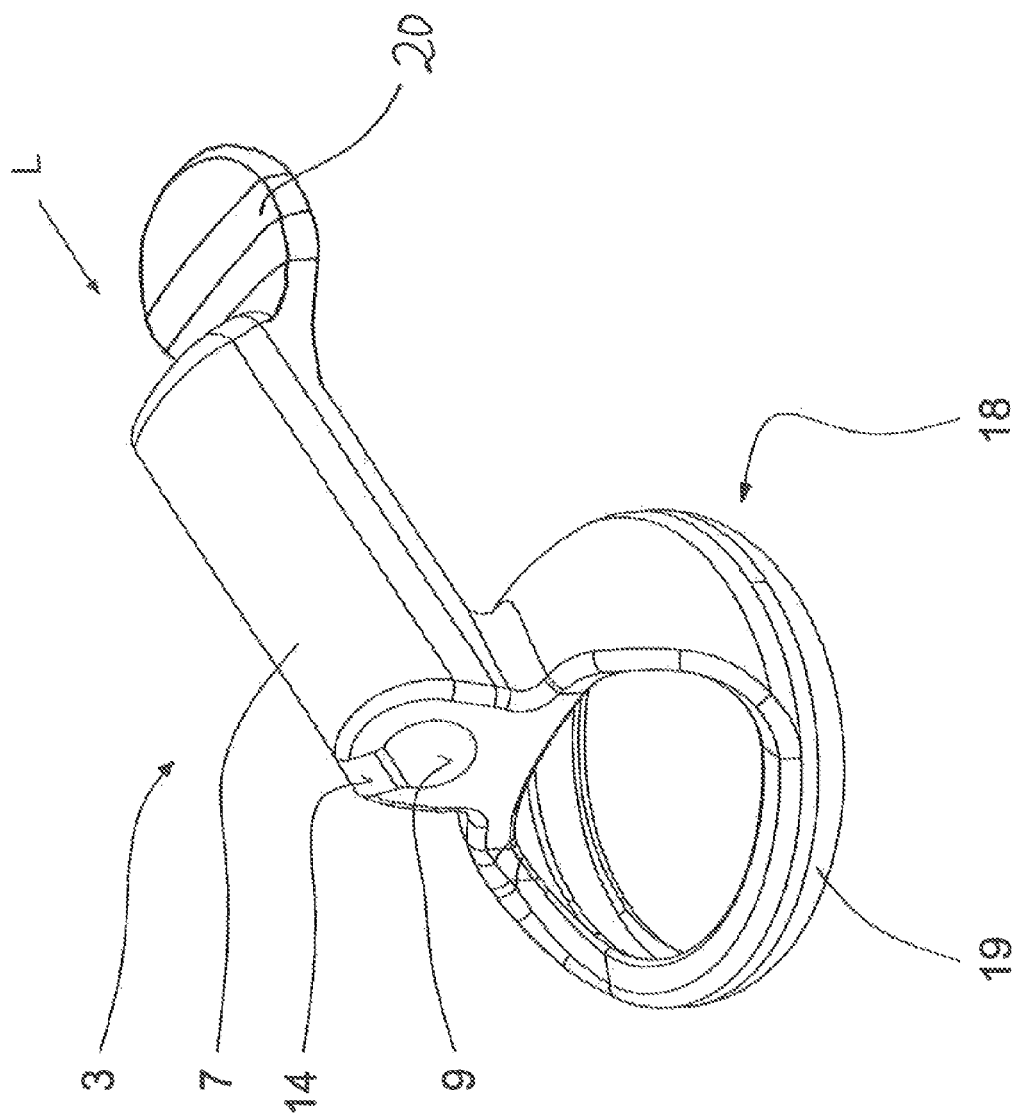
Figure 4:
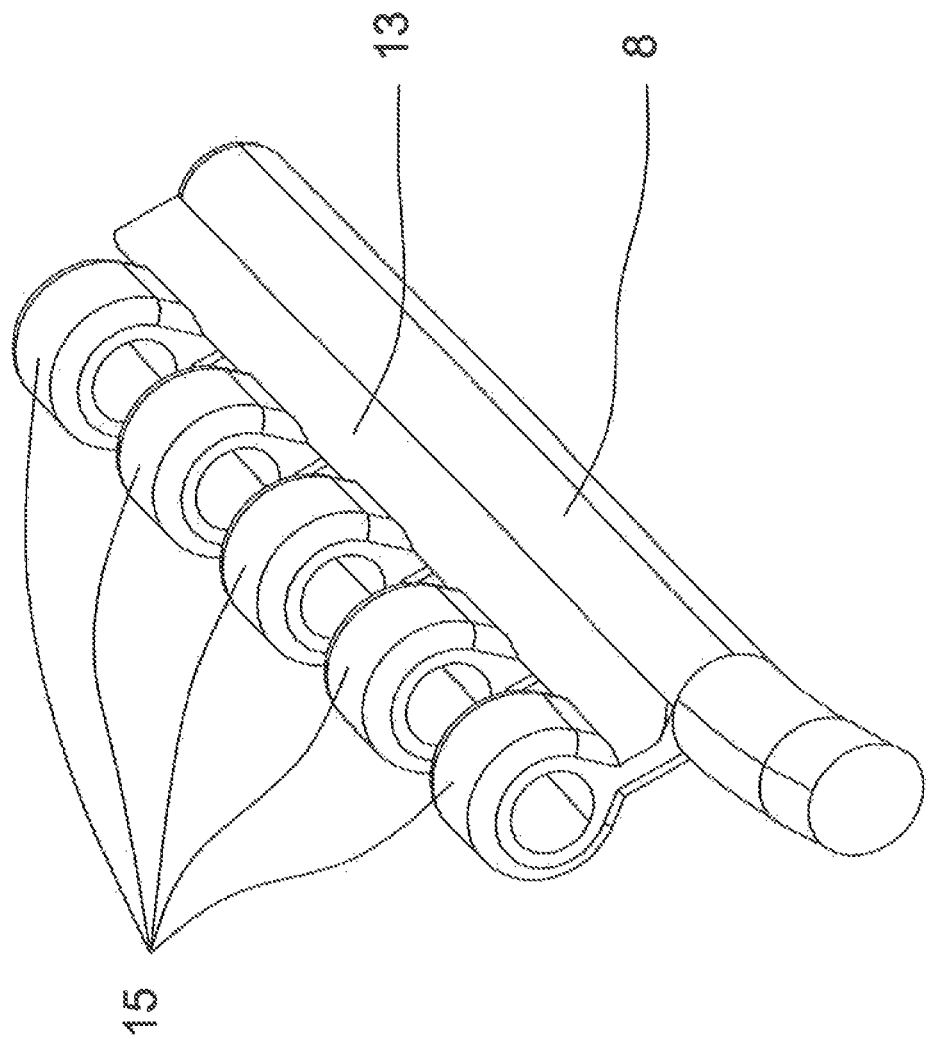
Figure 5:
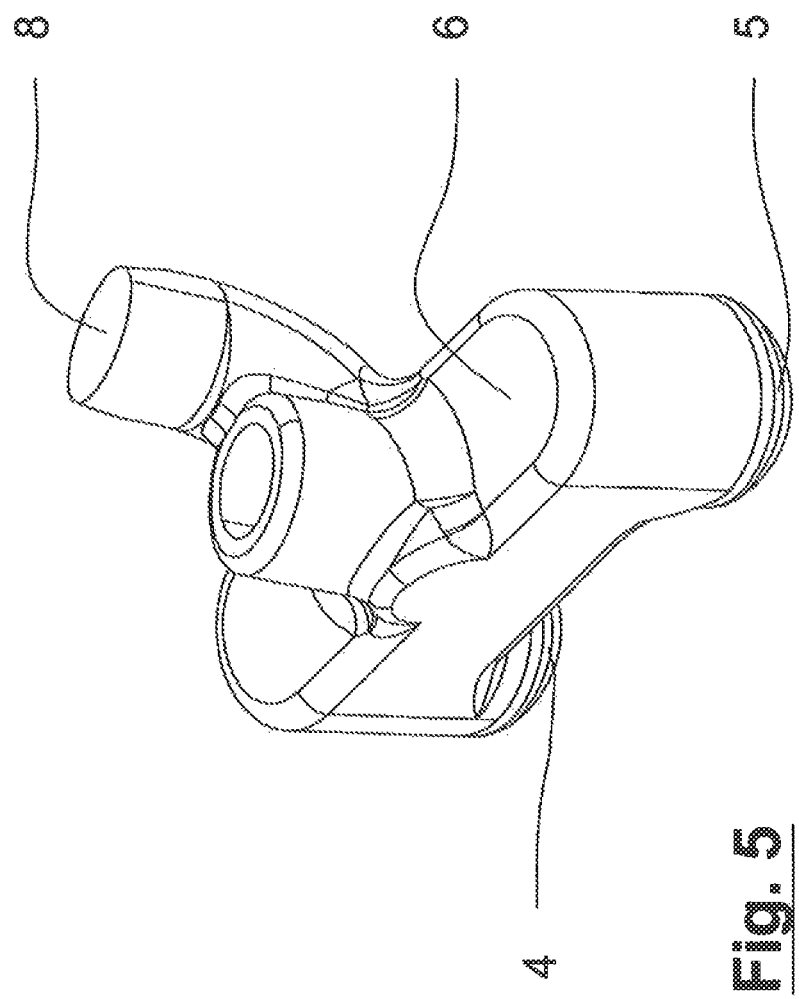
Figure 6:
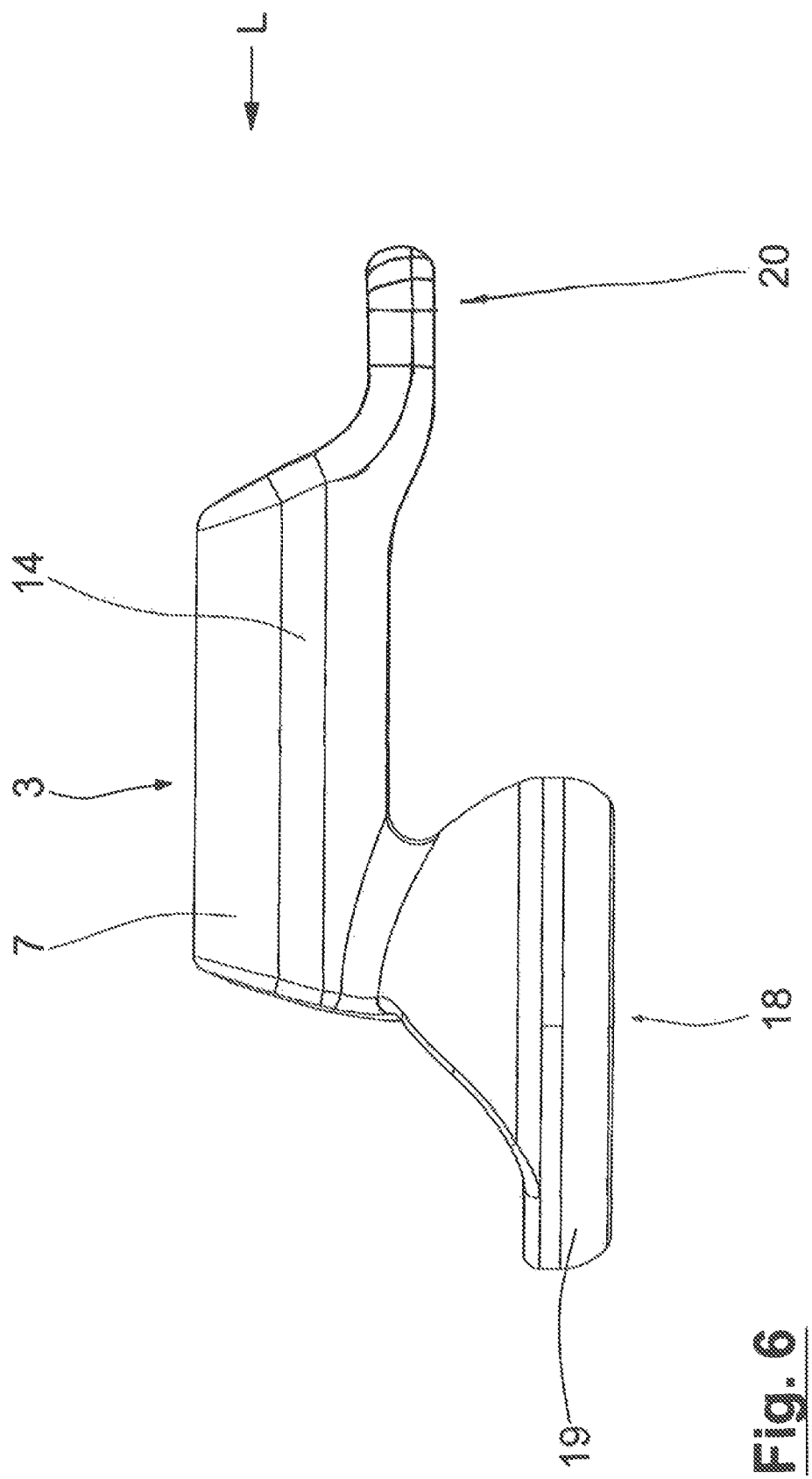
Figure 7:
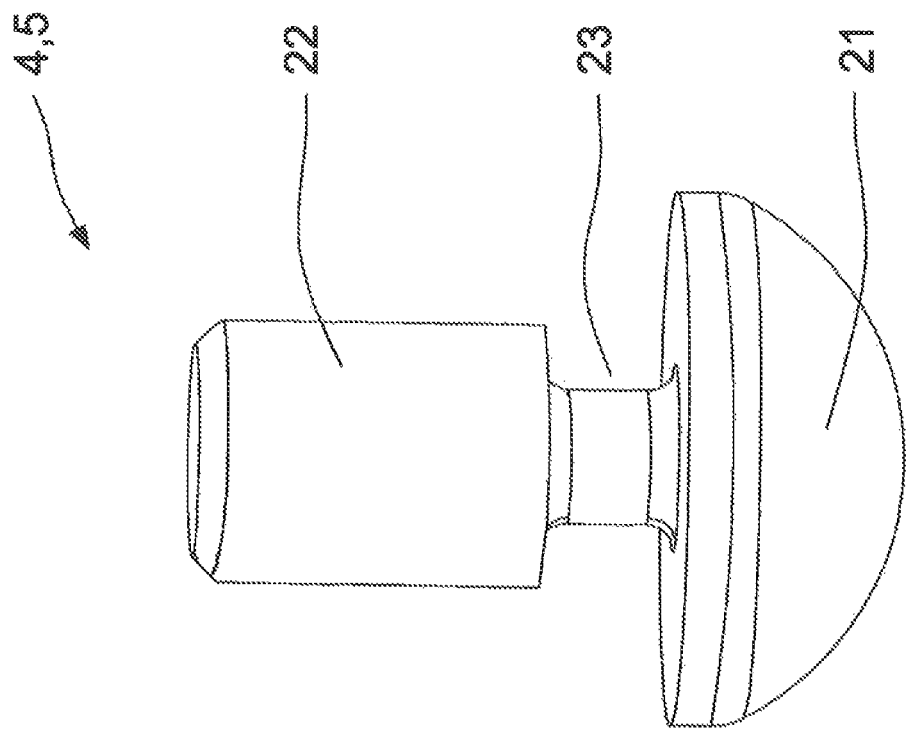
Figure 8:
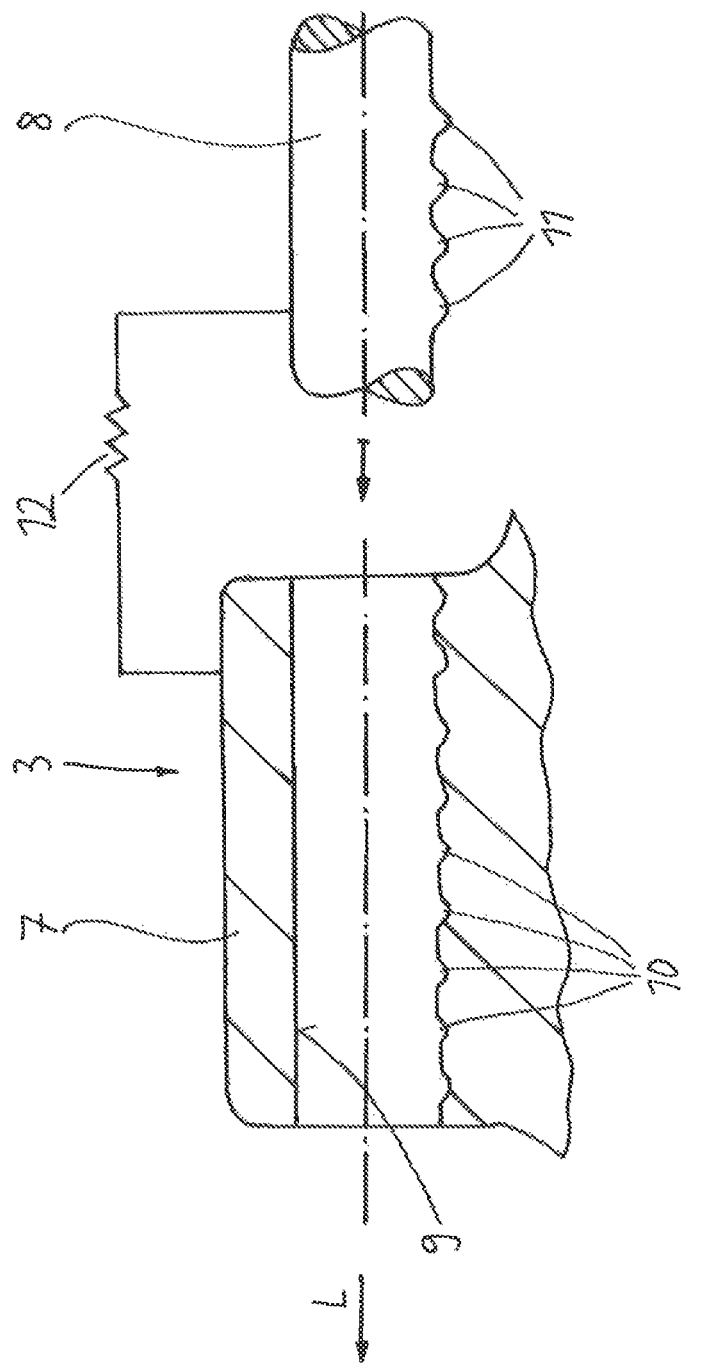
Figure 9:
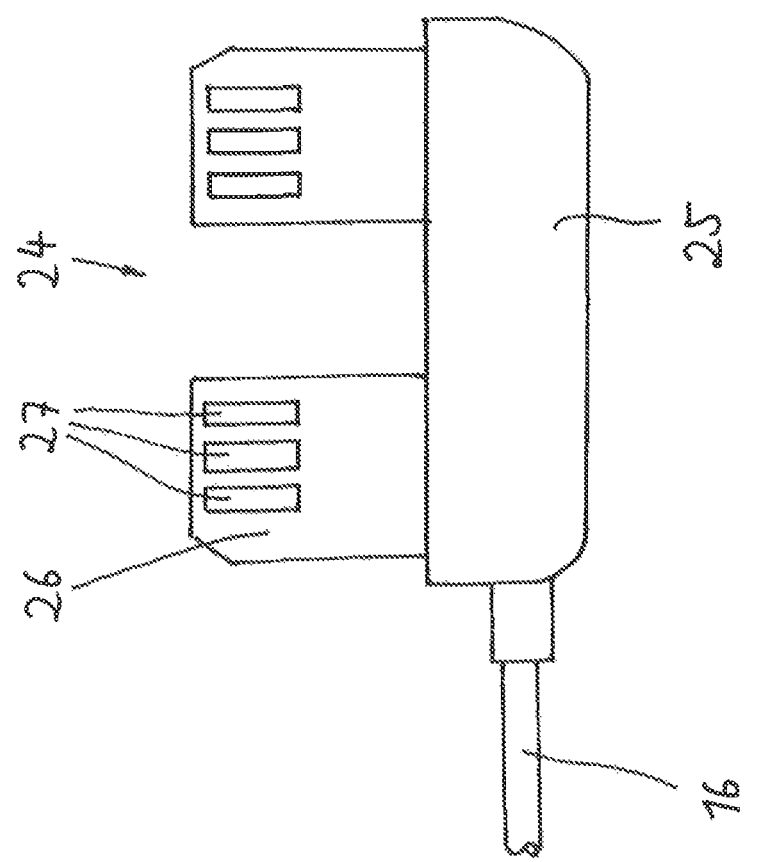

In the drawings an embodiment of the invention is depicted. It shows:

FIG. 1 in a perspective view an electrode arrangement according to the invention, FIG. 2 the view of a pinna (concha) in which an electrode arrangement according to FIG. 1 is inserted for the application of a transcutaneous stimulation stimulus, wherein here some parts of the electrode arrangement are not shown for sake of clearness of the depiction, FIG. 3 in a perspective view the holding element of the electrode arrangement according to FIG. 1, FIG. 4 in a perspective view a section of the holding bar of the electrode arrangement according to FIG. 1, FIG. 5 in a perspective view the electrode carrier including electrodes of the electrode arrangement according to FIG. 1, FIG. 6 in a side view the holding element of the electrode arrangement according to FIG. 1, FIG. 7 in a side view one electrode of the electrode arrangement according to FIG. 1, FIG. 8 schematically in a cross section view a part of the holding element as well as a part of the holding bar of the electrode arrangement, wherein the holding bar is not yet mounted, and FIG. 9 schematically a plug of the electrode arrangement by which the electrodes are supplied with current.

In FIG. 1 an electrode arrangement 1 is shown in form of an otoplastic, which electrode arrangement can be inserted in an ear 2 of a person, which ear is shown in FIG. 2, to carry out a transcutaneous electro stimulation of the skin surface in the area of the ear. Parts of the electrode arrangement 1 are visible in the FIGS. 3 to 6.

With the electrode arrangement 1 a transcutaneous electrical nerve stimulation can be conducted concretely upon a surface area of the ear. For this purpose the electrode arrangement comprises a stimulation electrode and a reference electrode (s. below), between which an electrical potential will be created; the means which are therefore necessary are known sufficiently in the state of the art, so that they don't have to be explained further here. Exemplarily it will be pointed and explicitly referred to DE 10 2005 003 735 B4 of the applicant.

The electrode arrangement 1 has a holding element 3 as an essential building component as well as a holding bar 8. The holding bar 8 carries an electrode carrier 6 at an axial end, which electrode carrier is provided with two electrodes 4, 5, that is to say with a stimulation electrode 4 and a (identical in construction) reference electrode 5. The electrode carrier 6 holds both electrodes 4, 5 on an exact desired distance and is developed as a bridge element between the electrodes 4, 5. The holding element 3 has a central section, which section is dominated from a linear guide 7. In this connection it is about a material section with a form like a bar, which section extends itself into a longitudinal direction L, in which material section a ring-shaped recess 9 is formed. At the front end of the linear guide 7 a resting part 18 is formed on; at the rear end a cheek rest 20 is formed on. The resting part 18 comprises a ring-shaped section 19; the cheek rest 20 is presently designed as a flat section and serves in addition as a stabilization of the resting of the electrode arrangement 1.

Here, it is essentially that the holding element 3 is able to shift the holding bar 8 linearly into the direction of the longitudinal axis L by the linear guide 7.

With that it will be possible to change the distance between the electrode carrier 6 and therefore the electrodes 4, 5 and especially the resting part 18 and to adjust it on a desired value.

This adjustment possibility will be used to shift the electrode arrangement after the placement in the ear 2 in such a way, that it can find good holding in the ear 2 during good wearing comfort.

For this it will be referred to FIG. 2. Here it can be seen that the electrode arrangement 1 has been placed into the ear 2 and has been set relatively to the holding element 3 by linear shifting of the holding bar 8 in such a way, that the electrode arrangement 1 has fixed itself elastically due to the topography of the ear 2. The electrode arrangement 1 has been precisely arranged into the Pinna P of the ear 2 in such a way that the electrode carrier 6 comes to lay in the area of the Cymba conchae Cy, while the resting part 18 with its ring-shaped section 19 overlies in the area of the Cavum conchae Ca. Accordingly, the ring-shaped section 19 comes to be put underneath of the Tragus T and the Crus helicis Cr.

Due to a spring flexibility (conditional upon the material) of the holding bar 8 respectively because of a spring element which is integrated in the case of requirement into the holding bar 8 (e.g. spring wire) the electrode arrangement 1 strains itself therefore after linear adjustment of the holding bar 8 relatively to the holding element 3 in an elastic way, so that a sufficient hold is given within the ear. As can be seen in FIG. 2, the ring-shaped design of the section 19 allows a substantially unhindered hearing.

Coming back to FIG. 1 once again, it can be seen that the holding bar 8 is equipped with means 13, 14 for preventing of rotation around the longitudinal axis relatively to the holding element 3. This means consist once of a lateral extension 13, which lateral extension is formed at the holding bar 8 and extends radial outwards from the holding bar 8. Furthermore, the means are formed by a slit-formed recess 14, which recess is machined into the holding element 3—extending itself into longitudinal direction L. Accordingly, the holding bar 8 including the lateral extension 13 can move in longitudinal direction L in the linear guide 7, but cannot rotate around the longitudinal axis L.

At the radial outward lying end of the lateral extension 13 there are several holding means 15 formed on in the form of ring-shaped structures, which structures serve to keep the cable 16 (preferably with a 3-wire Kevlar litz wire and surrounded with biocompatible mantle material) strain-relieved, which cable supplies the electrodes 4, 5 with power. The holding means 15 serve therefore as lugs for guiding the cable in which the cable 16 will be lead and strain-relieved. The cable 16 can thereby be injection moulded at the injection molding of the one-piece designed parts 8, 13 and 15. At the manufacturing of the electrode carrier 6 by injection moulding the cable 16 can be injection moulded analog to achieve a hermetical sealing of all seams.

The holding bar 8 comprises over an area a linear straight course, which course is approximately half until two third of the entire extension in longitudinal direction L. This is in profile basically correspondingly formed to the recess 9 in the holding element 3, thus presently circular. On this linear straight section a S-formed bent section connects—as connection section to the electrode carrier 6—which S-formed bent section has the function to lead down the electrode carrier 6 from the height, in which the linear guide 7 resides, to the skin surface which is to be stimulated. As already explained this has to occur in this way, so that the electrode carrier 6 presses elastically against the skin surface and preferably also produces incidentally a biasing force into the direction of the longitudinal axis L.

For this purpose it will be reverted to a material for the holding bar, which comprises the desired flexibility. It is also possible, that a spring element will be integrated into the bended respectively cranked section of the holding bar 8 (respectively over its whole extension). In this connection it can be for example a spring wire, which will be coated during the injection molding of the holding bar 8.

Thereby, the selection of the basic material, when indicated the integration of a spring element and the geometrical forming of the holding bar take place in a skilled way, so that a desired flexibility is at hand.

So, that a sufficient flexible pressing force occurs in the direction perpendicular to the skin surface which has to be stimulated, the electrode carrier 6 however will be held in a soft bendable connection relatively to the holding element around an axis, which is perpendicular to the longitudinal direction L—so that the electrode carrier 6 can adjust itself in an optimal way to the surface topography of the skin surface, which has to be stimulated—it is provided according to a special embodiment, that two grooving respectively insections 17 are placed laterally into the holding bar 8, which are in the area of the S-formed part of the holding bar 8 (s. for this FIG. 1 and FIG. 2). Thereby, the holding bar 8 becomes more bendable around an axis, which is perpendicular to the longitudinal axis (that is to say around the axis, which stands perpendicular on the plane of projection in FIG. 2), without that the flexibility of the holding bar 8 will be considerably affected perpendicular to the skin surface which has to be stimulated.

In FIG. 7 an electrode 4, 5 can be seen in the side view, which is fixed in the electrode carrier 6 by injection moulding. The electrode comprises a contact section 21, which is provided for establishing of contact with the skin which is to be stimulated. Furthermore, the electrode 4, 5 has a pin-shaped anchoring section 22, which anchoring section will be fixed into the material of the electrode carrier 6. Between contact section 21 and anchoring section 22 there is an insection 23 (groove), which insection forms an axial undercut, which undercut takes care for a form-fitted axial fixation of the electrode 4, 5 in the electrode carrier 6. It can also be provided—which is not displayed though—that at one circumferential position of the pin-shaped anchoring section 22 a flat area is arranged, so that after the injection molding of the electrode 4, 5 at the manufacturing of the electrode carrier 6 also a rotation will be prevented around the longitudinal axis of the electrode 4, 5. The electrodes 4, 5 consist preferably of a titan-aluminum-composition (TiAl6V4).

In FIG. 8 a further relevant aspect of the electrode arrangement 1 is shown schematically. In fact it is basically possible to tolerate the measures of the recess 9 in the holding element 3 and of the linear part of the holding bar 8 in such a way, that due to a press fit an adequate resistance is given against the linear shift of the holding bar 8 relatively to the holding element 3, i. e. a linear shifting without too large forces is given, however also a sufficient holding force is given, so that the electrode arrangement will be held in position in the ear after its adjustment.

An embodiment, as FIG. 8 shows, is however advantageous. Accordingly, latching means 10, 11 are provided in the linear guide 7, which latching means allow it, to arrange the holding bar 8 in a latched manner relatively to the holding element 3 in defined positions. On this the recess 9 of the linear guide 7 comprises at least at one circumferential position a number of equidistanced groove-shaped recesses 10 according to the embodiment of FIG. 8. Correspondingly, the holding bar 8 comprises a number of protrusions 11, which protrusion are arranged in identical intervals. Naturally, also the recesses can be arranged in the holding bar 8 and the protrusions in the linear guide 7 in the opposite way. Accordingly the parts 3 and 8 can be latched relative to another in a number of latching positions.

If the holding bar 8 will be inserted into the recess 9 (s. arrow in FIG. 8), latching positions accrue due to the material flexibility at the passing of the protrusions 11 on the groove-shaped recess 10, in which latching positions the linear guide 7 finds respective persistence conditions, which can only be overcome by application of a sufficient force into the direction of the longitudinal axis L. Accordingly, the holding bar 8 can be placed in a desired latching position in the linear guide 7. Therefore a defined, stepwise resistance will be realized relatively to the holding element 3 at the translational shifting of the holding bar 8.

Only schematically illustrated are spring means 12, which are effective between the holding bar 8 and the holding element 3 and which can produce a spring biased effect, to keep the electrode carrier 6 including the electrodes 4, 5 elastically biased. The spring means 12 can be for example an elastic strap, which elastic strap is effective in the linear shifting direction of the linear guide 7.

In FIG. 9 a plug 24 is visible, by which the mechanical and electrical contact will be established to a (not displayed) stimulation device. In a base body 25 a board 26 will be fixed, likewise the cable 16. Every plug of the board 26 has three contact points 27. The plug 26 will be plugged in into the stimulation device. Via the contact points 27 and the accordant counter piece within the stimulation device the electrical contact will be established. By a non-symmetrical design a not correct plugging of the plug into the stimulation device can be prevented.

LIST OF REFERENCES

1 Electrode arrangement
2 Ear
3 Holding element
4 Electrode (stimulation electrode)
5 Electrode (reference electrode)
6 Electrode carrier
7 Linear Guide
8 Holding bar
9 Recess
10, 11 Latching means
10 Groove-shaped recess
11 Protrusion
12 Spring means
13, 14 Means for preventing of rotation
13 Lateral extension
14 Recess
15 Holding means
16 Cable
17 Notch/insection
18 Resting part
19 Ring-shaped section
20 Cheek rest
21 Contact section
22 Pin-shaped anchoring section
23 Insection
24 Plug
25 Base body
26 Board
27 Contact Point
L Longitudinal axis
Ca Cavum conchae
Cy Cymba conchae
T Tragus
Cr Crus helicis
P Pinna

The invention claimed is:

1. An electrode arrangement for the application of a transcutaneous electric stimulation stimulus onto the surface of a section of the human ear, comprising:
   a holding element arranged at or in the ear;
   at least one electrode arranged in an electrode carrier;
   the holding element comprises a resting part, which is designed and provided for the application onto the Cavum conchae (Ca) of the ear;
   the holding element comprises a linear guide in which a holding bar is arranged linear movably in the direction of a longitudinal axis of the holding element; and
   the electrode carrier is arranged at the holding bar.

2. The electrode arrangement according to claim 1, wherein the electrode carrier is arranged at an axial end of the holding bar.

3. The electrode arrangement according to claim 1, wherein the electrode carrier is an electrode head, and comprises at least one stimulation electrode and at least one reference electrode.

4. The electrode arrangement according to claim 1, wherein the linear guide of the holding element is formed by a recess which has a circular shape, along the longitudinal axis in a section perpendicular to the longitudinal axis, the holding bar comprises a circular shaped cross section at least along a part of its extension.

5. The electrode arrangement according to claim 1, wherein latching means is arranged between the linear guide and the holding bar, so that the holding bar can be arranged lockable relatively to the linear guide along the longitudinal axis in predetermined relative positions.

6. The electrode arrangement according to claim 5, wherein the latching means comprises at least one groove-shaped recess within the linear guide and at least one protrusion within the holding bar, which extends radial outward, the protrusions are designed as a wave path with a plurality of radial elevations.

7. The electrode arrangement according to claim 1, wherein a spring means is arranged between the linear guide and the holding bar, so that the holding bar can be biased elastically relative to the linear guide in the direction of the longitudinal axis.

8. The electrode arrangement according to claim 1, further comprising a means for preventing rotation of the holding bar relatively to the linear guide around the longitudinal axis.

9. The electrode arrangement according to claim 8, wherein the means for preventing rotation is formed by a lateral extension, which is radial extending from the holding bar, wherein in the linear guide a corresponding recess for the lateral extension is arranged.

10. The electrode arrangement according to claim 9, wherein the lateral extension as well as the recess have a square form in a section perpendicular to the longitudinal axis.

11. The electrode arrangement according to claim 1, wherein the holding bar has an S-form design in its axial end region, in which end region the electrode carrier is arranged.

12. The electrode arrangement according to claim 1, wherein the holding bar is reinforced in its axial end region with a spring element, with a spring wire or a leaf spring, in which end region the electrode carrier is arranged.

13. The electrode arrangement according to claim 1, wherein the holding bar comprises at least one collateral notch or at least one collateral insection in its axial end region, in which the electrode carrier is arranged, to reduce the bending stiffness of the holding bar in the axial end region around a direction, which is perpendicular to the longitudinal axis.

14. The electrode arrangement according to claim 1, wherein the resting part has a circular ring-shaped section or an oval ring section.

15. The electrode arrangement according to claim 1, wherein the holding element comprises a cheek rest, which is arranged at the holding element at the end of the electrode arrangement remote from the electrode carrier.

* * * * *